Figure 1:
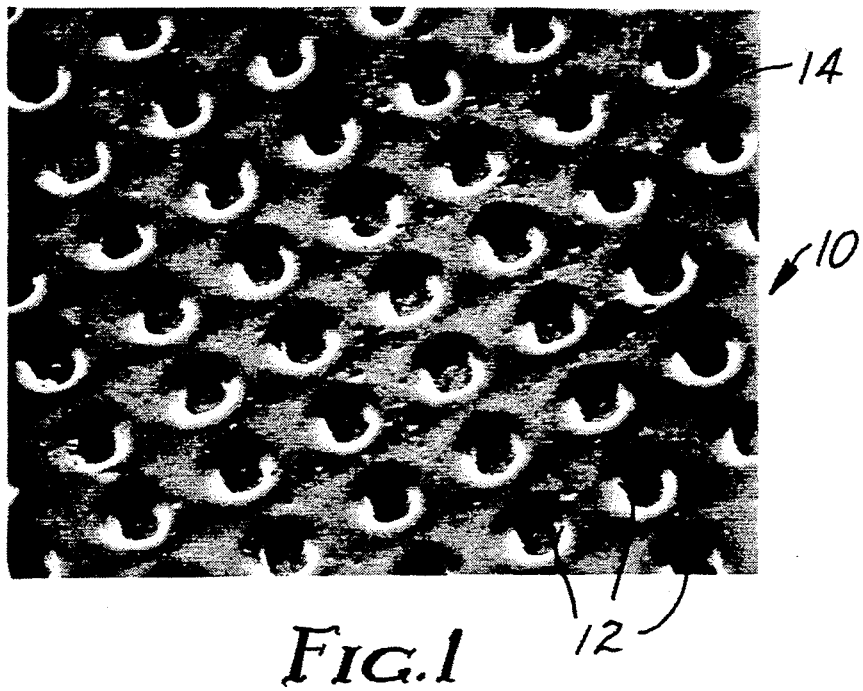

United States Patent [19]
Velasquez et al.

[11] Patent Number: 5,192,548
[45] Date of Patent: Mar. 9, 1993

[54] DEVICE

[75] Inventors: David J. Velasquez; Peter D. Hodson; Clyde D. Calhoun, all of St. Paul, Minn.

[73] Assignee: Riker Laboratoires, Inc., St. Paul, Minn.

[21] Appl. No.: 516,327

[22] Filed: Apr. 30, 1990

[51] Int. Cl.$^5$ ............................................. A61F 13/00
[52] U.S. Cl. ................................ 424/443; 128/203.12; 128/204.13
[58] Field of Search .................... 424/443; 128/203.12, 128/204.13

[56] References Cited

U.S. PATENT DOCUMENTS

| | | | |
|---|---|---|---|
| 3,927,995 | 8/1976 | Tzuk et al. | 424/447 |
| 3,948,264 | 4/1976 | Wilke et al. | 128/203.15 |
| 3,971,377 | 7/1976 | Damani | 128/200.47 |
| 4,147,166 | 4/1979 | Hansen | 128/203.15 |
| 4,735,358 | 4/1988 | Morita et al. | 239/1 |

FOREIGN PATENT DOCUMENTS

| | | |
|---|---|---|
| 69715 | 6/1982 | European Pat. Off. |
| 79478 | 10/1982 | European Pat. Off. |
| 166294 | 6/1985 | European Pat. Off. |
| 239802 | 2/1987 | European Pat. Off. |
| 224335 | 6/1987 | European Pat. Off. |
| 2837040 | 2/1980 | Fed. Rep. of Germany |
| 25422 | 1/1984 | Fed. Rep. of Germany |
| 8806288 | 10/1988 | Fed. Rep. of Germany |
| 2516387 | 5/1983 | France |
| WO85/01880 | 5/1985 | PCT Int'l Appl. |
| 1479283 | 7/1973 | United Kingdom |
| 2061735 | 5/1981 | United Kingdom |
| 2102295 | 7/1982 | United Kingdom |
| 2144997 | 7/1982 | United Kingdom |
| 2108390 | 9/1982 | United Kingdom |
| 2122903 | 2/1983 | United Kingdom |
| 2166957 | 2/1983 | United Kingdom |
| 2162152A | 1/1986 | United Kingdom |

Primary Examiner—Paul R. Michl
Assistant Examiner—Leon R. Horne
Attorney, Agent, or Firm—Gary L. Griswold; Walter N. Kirn; Douglas E. Reedich

[57] ABSTRACT

A sheet material comprising discrete depressions which are at least partially filled with micronized medicament and which are useful as or in a drug delivery device. This sheet material is useful in devices which provide for aerosolization of the medicament, for delivery to a patient by inhalation.

22 Claims, 5 Drawing Sheets

DEVICE

TECHNICAL FIELD

This invention relates to a delivery device for administration of a medicament by inhalation.

BACKGROUND OF THE INVENTION

Asthma and other respiratory diseases have long been treated by the inhalation of appropriate medicament. For many years the two most widely used and convenient choices of treatment have been the inhalation of medicament from a drug solution or suspension in a metered dose pressurised inhaler (MDI), or inhalation of powdered drug generally admixed with an excipient, from a dry powder inhaler (DPI). With growing concern being voiced over the strong link between depletion of the earth's ozone layer and chlorofluorocarbon (CFC) emissions, the use of these materials in pressurised inhalers is being questioned and interest in DPI systems has been stimulated.

Existing single and multiple dose dry powder inhalers use either individual pre-measured doses or bulk powder reservoirs. In both cases only fairly large quantities (e.g., several hundred micrograms) can constitute a dose due to problems associated with accurately transferring a measured small quantity of powder either into a capsule, or from a bulk reservoir within an inhaler. With potent drugs this introduces the necessity to add excipients, such as lactose powder, to increase the quantity of powder to be measured. These excipients are undesirable, however, as they pose subsequent powder deagglomeration problems and cause dryness in the patient's mouth. In addition, the use of individual pre-measured doses tends to lead to the production of bulky inhalation devices.

Dry powder inhalers in which the medicament is introduced into the device from a capsule are disclosed in U.S. Pat. Nos. 3,948,264, 3,971,377 and 4,147,166 and British Patent No. 1479283. Dry powder inhalers having a reservoir of dry powder from which unit doses are transferred to a chamber by means of a delivery system, such as a rotating perforated membrane in which the perforations are filled with powder from the reservoir, are disclosed in British Patent Application Nos. 2102295 and 2144997 and European Patent Application Nos. 69715, 79478 and 166294.

U.S. Pat. No. 4,735,358, European Patent Application No. 239802 and British Patent Application Nos. 2108390, 2122903 and 2166957 disclose vaporisers in which active substances capable of modifying the local atmosphere e.g. insecticides, deodorants and aromatics are vaporised for dispersion to the atmosphere. The active substance is carried or impregnated on a belt or tape consisting of a suitable base material, in such a state that vaporisation can be conducted at ambient temperature or under administration of localised heating by a vaporising head. The substance is maintained in an inactive condition until the belt passes over the vaporising head whereby thermal release is achieved. The belt may be moved to the vaporising head by hand or at a fixed speed by a motor driving feed means through a reduction gear and is taken up by a shaft or spindle. In one embodiment the belt is contained in a cassette to provide a re-usable device, the cassette being engaged by drive means and having a suitable aperture for the belt to pass across the vaporising head. None of the vaporisers disclosed are designed or suitable for delivering a predetermined unit dose of powdered solid medicament to a patient.

It has now been found that predetermined doses of a dry powder may be stored in and dispensed from a sheet material having drug-filled depressions in the surface thereof.

BRIEF SUMMARY OF THE INVENTION

This invention provides a flexible sheet material comprising a plurality of discrete depressions in at least one surface thereof, each of the depressions having a depth of about 5 to 500 μm, but less than the thickness of the sheet material, and an opening at the surface of the sheet material of about 10 to 500 μm across, a substantial number of the depressions being at least partially filled with micronized medicament, and the area of the surface of the sheet material between the depressions being substantially free of micronized medicament. Preferably the sheet material will be in the form of an elongate strip or tape.

The sheet material of the invention is a convenient medicament-carrying substrate which allows for aerosolization of the medicament in a relatively deagglomerated state so that such may be administered by inhalation. A variety of means may be employed to aerosolize the medicament including application of an impaction force on the back-side of the sheet material. The sheet material of the invention is particularly useful with medicaments having high potency for either local treatment of, for example, the lung or systemic treatment.

BRIEF DESCRIPTION OF THE DRAWINGS

The invention will be better understood by reference to the following drawings wherein:

FIG. 1 is a photograph of the blank sheet without powder contained in the depressions thereof;

FIG. 2 is a partial enlarged sectional view of FIG. 1;

FIG. 3 is a cross-sectional view of a schematic of a sheet with powder contained in the depressions thereof;

FIG. 4 is a photograph of the top plan of the sheet with powder having been applied and generally removed between depressions;

FIG. 5 is a partial enlarged view of FIG. 4;

FIG. 6 is a photograph of the top plan of the sheet with powder having been removed more rigorously by an additional treatment from the top surface between the depressions;

FIG. 7 is a partial enlarged view of FIG. 6;

FIG. 8 is a photograph of the sheet from which powder has been aerosolized by impaction on the back-side of the sheet; and FIG. 9 is a schematic of a device for applying powder to the sheet.

DETAILED DESCRIPTION OF THE INVENTION

As illustrated in FIGS. 1 and 2 flexible sheet material 10 comprises a substantially regular array of depressions or microdimples 12 formed in the top surface of a layer of polymeric material 14. Depressions 12 are generally truncated cones in the illustrated embodiment, but may alternatively be of any suitable configuration for holding micronized medicament including generally truncated pyramids, partial hemispheres and tetrahedrons and other geometric configurations as well as non-geometric configurations. Presently preferred depressions have a sidewall angle of about 15°–20° to the vertical. The array of depressions may take any form or pattern and need not be regular (i.e., the array may be irregular in appearance).

The depressions generally have a depth of about 5 to 500 μm and an opening at the surface of the sheet material of about 10 to 500 μkm across with respect to the major axis of the opening. In the case of the depressions having generally circular openings such as truncated cones or partial hemispheres, for example, the major axis discussed above is, in fact, the diameter of the circular opening. Preferred depressions have a depth of about 5 to 150 μm and an opening (e.g., diameter in the case of truncated cones or partial hemispheres or the like) at the surface of the sheet material of about 50 to 200 μm. The depressions generally will be spaced about 20 to 2000 μm, preferably about 50 to 200 μm, from one another. Preferably the depressions will number from about 500 to 15,000 per $cm^2$ of the sheet material. The volume of each depression and the spacing or number of the depressions will depend upon the potency of the medicament and the area of the sheet material intended to represent a single dose of the medicament. Preferably, the sheet material will have a substantially uniform depression volume per unit area.

Figure 3:
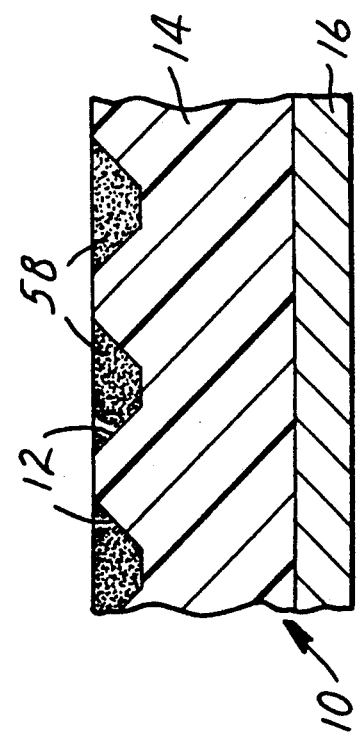

As illustrated in FIG. 3 sheet material 10 may further comprise a support layer of paper 16. The layer of polymeric material 14 has been laminated or melt-bonded to or extruded onto the support layer. Other support layers may be formed of non-wovens or polymers such as polyester.

The layer of polymeric material 14 may comprise any suitable polymer such as polyethylene, polypropylene, polyester, polytetrafluoroethylene and cellulose. Polyethylene is preferred. The layer of polymeric material will be typically about 25 to 1000 μm in thickness.

The sheet material may be formed of a single material such as polypropylene. The support layer is not required in such an embodiment since the sheet material even without the support layer will exhibit sufficient integrity and durability.

A preferred sheet material 10 is prepared using polyethylene-coated kraft paper available from Schoeller Company.

The depressions should have a depth such that they do not form pores extending through the entire thickness of the sheet material.

Figure 4:
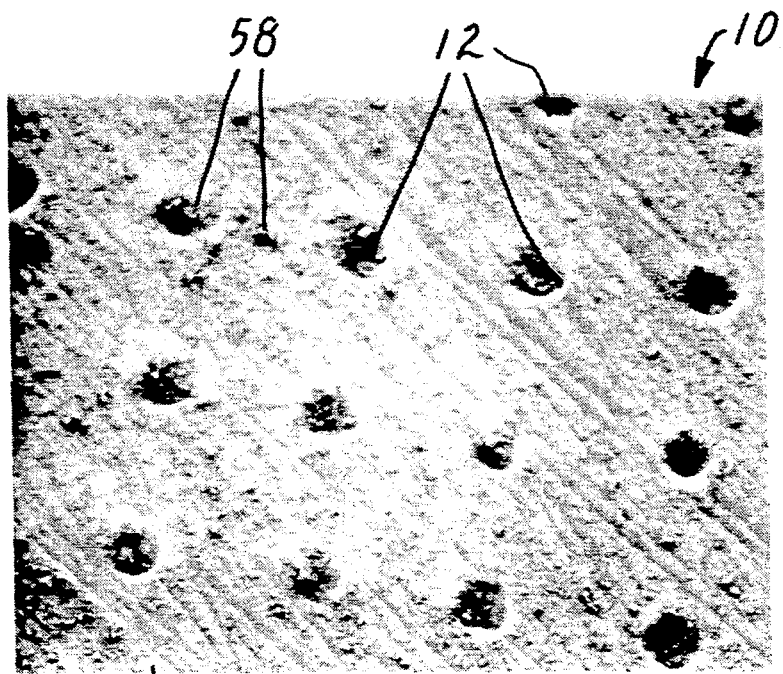
Figure 5:
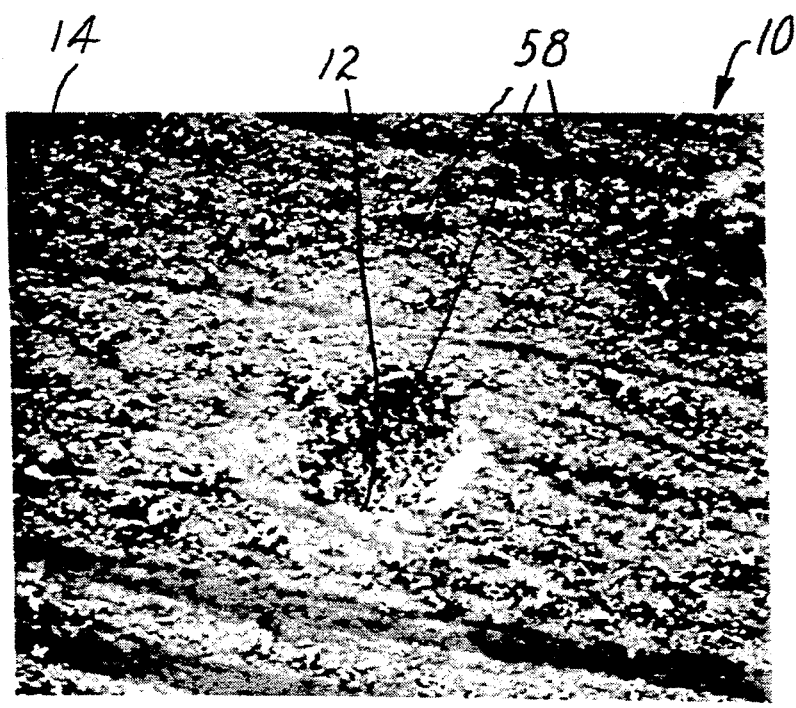

FIGS. 4 and 5 illustrate sheet material 10 after coating of the top surface of the sheet material with micronized drug 58 followed by general removal of excess drug. The bristles of a camel hair brush were dipped into micronized drug then brushed back and forth across the top surface of the sheet material 10 in order to fill the depressions 12 with micronized drug 58. The same brush was then used to brush away obvious portions of excess drug from areas of the top surface between the depressions 12.

Figure 6:
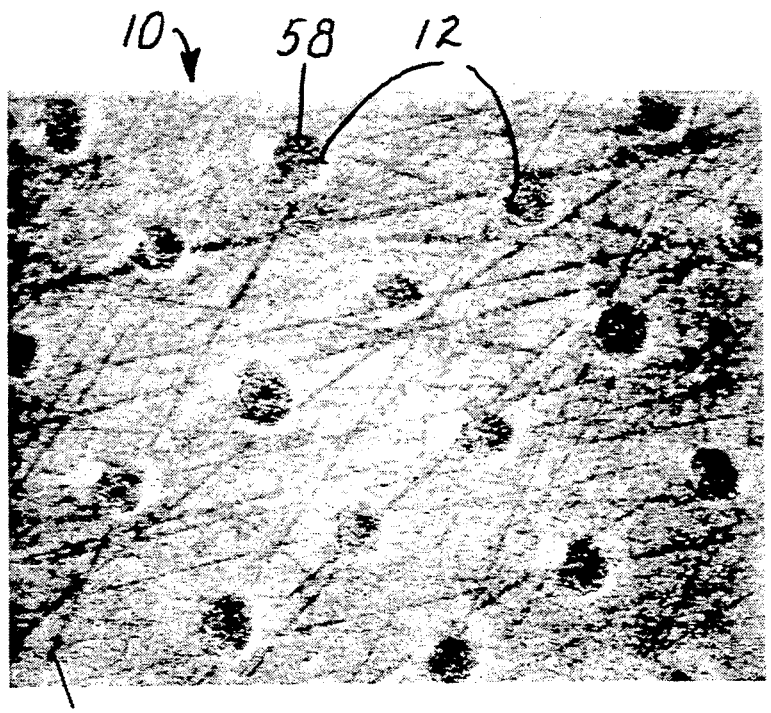
Figure 7:
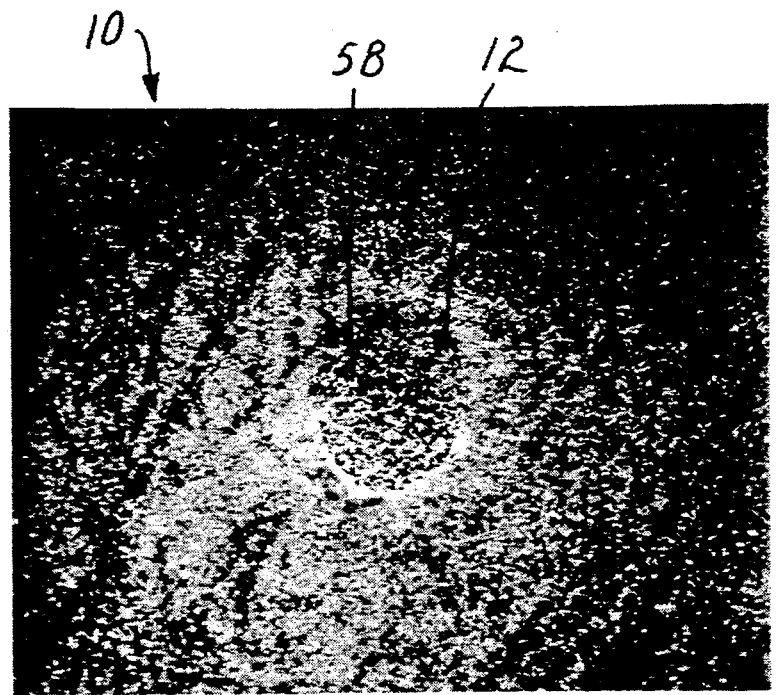

FIGS. 6 and 7 illustrate sheet material 10 after micronized drug has been removed more rigorously from the top surface of the sheet material in the areas of the top surface between the depressions 12. Sheet material 10 was coated with micronized drug and obvious portions of excess drug were removed as described for FIGS. 4 and 5. The top surface of the sheet material 10, now loaded with micronized drug 58, was scraped, first in one direction and then in the opposite direction, e.g., from left to right and then from right to left, with the edge of a razor blade held at approximately a 45 degree angle with respect to the top surface. A silicone rubber mat was then laid on the top surface of the sheet material 10 and contact between the mat and the top surface of the sheet material was provided by rolling the mat with a hand roller first in one direction then in the direction perpendicular to the first, e.g., from left to right then from top to bottom.

The coating process in respect of FIGS. 4–7 was performed by hand. Alternatively, the coating process may be performed using a device of a type illustrated in FIG. 9 which will be discussed in greater detail below.

Figure 8:
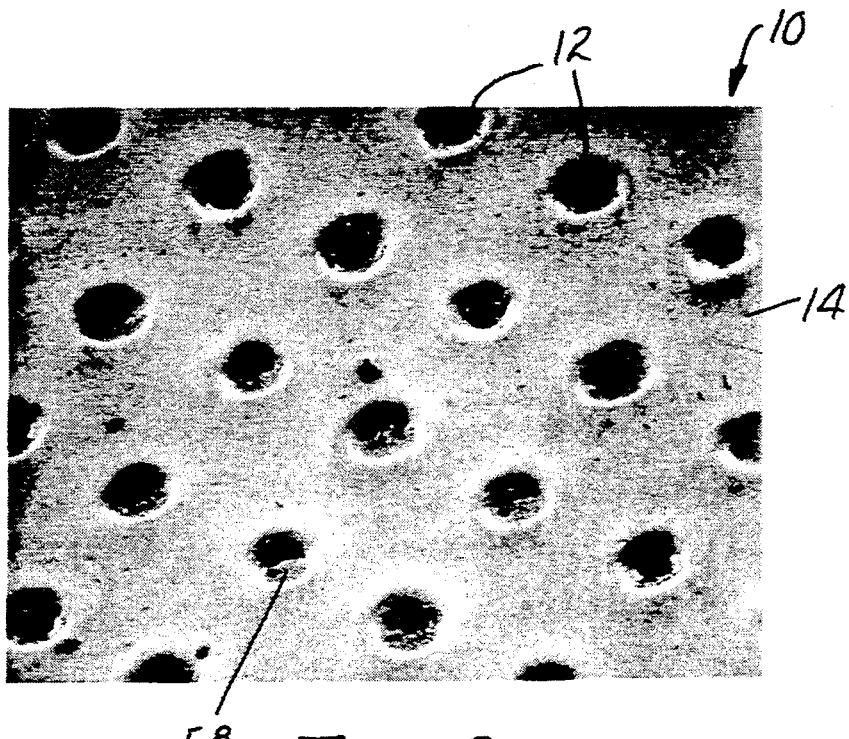
Figure 2:
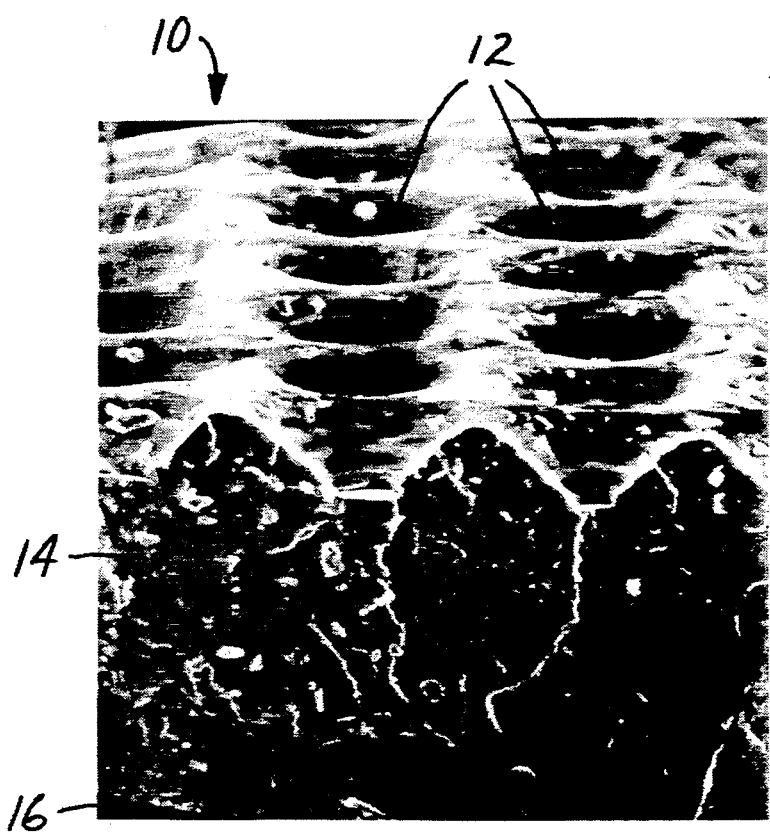

FIG. 8 illustrates an area of the sheet material 10 after micronized drug contained in the depressions 12 has been aerosolized by application of an impaction force (via a spring leaf driven hammer) upon the back-side of a support upon which sheet material was placed.

Figure 9:
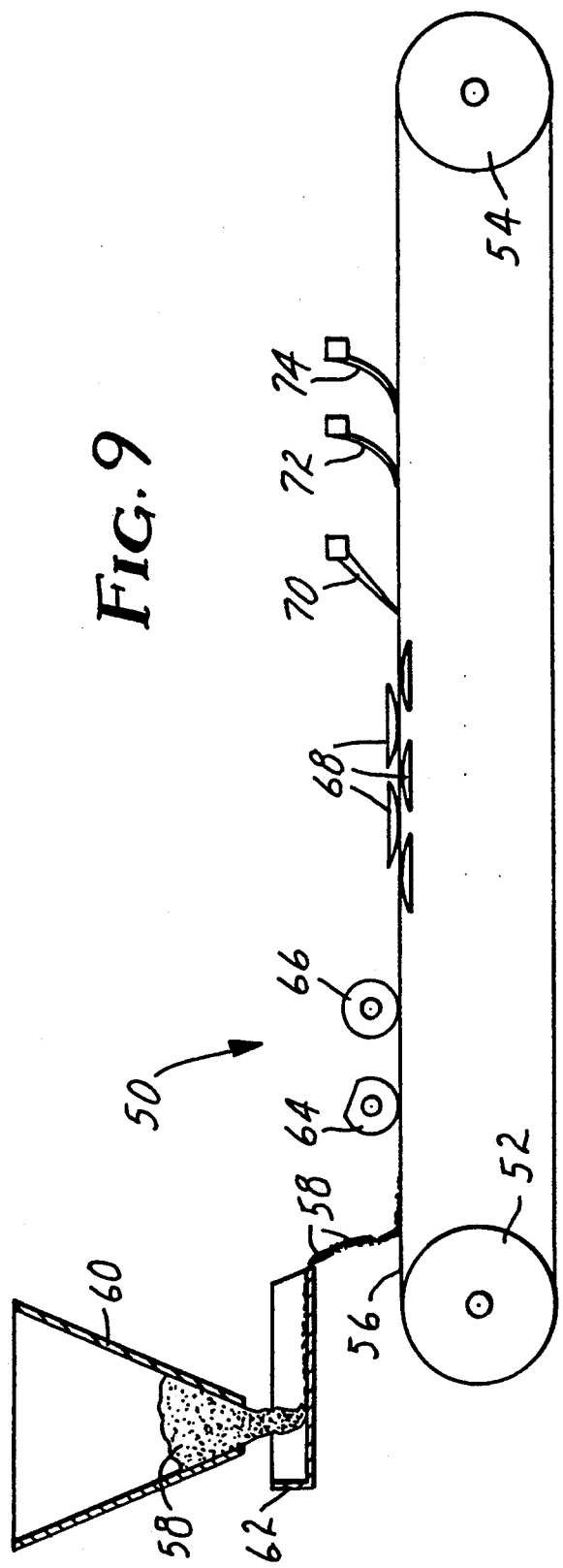

The coating device 50 illustrated in FIG. 9 comprises rollers 52 and 54 about which a closed loop of sheet material 56 travels. Micronized drug 58 contained in powder feed hopper 60 passes through vibratory feed 62 onto sheet material 56. Driven rollers 64 and 66 assist in spreading micronized drug 58 out over the surface of sheet material 56. A portion of the surface of driven roller 64 may be flattened to help prevent build-up of micronized drug 58 behind it.

Curved slats 68 function to smear the micronized drug 58 out over the surface of sheet material 56. Stainless steel blade 70 and acetate scraper blades 72 and 74 serve to remove the excess micronized drug 58 which is not contained within the depressions on the top-side of sheet material 56. It is preferred that a major portion of the micronized medicament originally filled into the depressions remain after the top surface of the sheet material has been scraped to remove the residual medicament contained on the surface of the sheet material between the depressions.

Sheet material 56 which is coated using device 50 is then preferably rolled between two sheets of silicone rubber using a plastic roller (not illustrated). The silicone rubber, since it has a high affinity for surface particles, removes most of the residual micronized drug not contained within the depressions but instead situated on the top surface of the sheet material between the depressions as well as on the back-side of the sheet material. Alternatively, a thin polymeric film such as that available under the trade designation Saran TM from The Dow Chemical Company may be used to remove residual particles through attraction resulting from their static charge.

While not wishing to be bound to any particular theory, it is believed that the micronized medicament is held within the depressions by a combination of electrostatic attraction, Van der Waals forces, physical attraction and, depending upon the configuration of the depression itself, mechanical binding or wedging.

As the packing density of the micronized medicament in the depressions may have influence on the form and amount of medicament released from the sheet material during the aerosolization process, care should be taken to assure that the packing density remains substantially uniform during the coating process.

The opening and depth dimensions and the spacing of the depressions influence how much micronized medicament the sheet material can carry per unit area for a given degree of compression of the medicament during loading or coating. Further, depression depth may influence the degree to which medicament is released from the sheet material and its relative state of agglomeration or unagglomeration. Using albuterol sulfate with a mean particle size of 1.7 μm and for single impactions of strength appropriate to an inhaler on areas of about 2 to 10 cm² of sheet material (see discussion below for disclosure of a device which may be used) the following was observed. The percentage of medicament retained on the sheet material or tape decreases as depression depth increases, this being about 95% at 14 μm, about 60% at 28 μm and about 35% at 45 μm. Further, the respirable fraction (i.e., the percentage of drug which is in particles of aerodynamic diameter of equal to or less than about 6.4 μm) similarly decreases as depression depth increases, this being about 65% at 14 μm, about 30% at 28 μm and about 10% at 37 μm. These two trends result in the proportion of total medicament released in particles of respirable size remaining generally similar for the depression depths studied (this being about 5 to 15% of total medicament).

Depressions 12 may be formed in the sheet material 10 by any suitable technique such as micro-imprinting using a photolithographically-patterned magnesium alloy plate or other micro-machined plate. Other conventional techniques which may be used are optical imaging or laser imaging.

As an illustrative example a sheet material according to the present invention has been prepared using a photolithographically produced etched magnesium alloy master plate having an array of pyramidal-shaped protuberances numbering about 1550 per cm² wound about a steel roller. The roller was heated to about 225° F. using oil. The polyethylene surface of polyethylene-coated kraft paper (commercially available from Schoeller Company) was pressed against the surface with a rubber or steel nip roll, also heated with oil and hydraulically pressurized against the patterned roll. The force will typically be about $5 \times 10^{-3}$ pounds ($2.3 \times 10^{-3}$ kg) per depression.

The sheet material having depressions therein may be prepared in any convenient width followed by slitting if desired to provide, for example, an elongate strip or tape. Preferably, the ratio of length:width is greater than 5:1, more preferably greater than 10:1 and most preferably between 100:1 and 1000:1. Preferably the tape will have a width of about 0.5 to 3 cm and more preferably about 1 to 2 cm.

The sheet material of the invention is particularly suited for delivering medicaments for inhalation by a patient. The sheet material preferably will provide regular release of the medicament when exposed to the force used to aerosolize the medicament. In a preferred embodiment of an aerosol device, the micronized medicament is aerosolized in an unagglomerated state by impaction on the back-side of the sheet material. Preferred devices for aerosolizing the medicament are disclosed in U.S. application Ser. No. 07/516,328, filed of even date now abandoned and commonly assigned, incorporated herein by reference. Suitable devices employing means other than impaction to aerosolize the medicament from the sheet material are also disclosed in said application. The sheet material will be preferably in the form of a tape which is contained within a cassette and is driven by a spiked idler with the tape containing appropriate apertures or is more preferably driven using a belt as described in said application.

Suitable medicaments for use in the invention include any drug or drugs which may be administered by inhalation which is a solid or may be incorporated in a solid carrier. Suitable drugs include those for the treatment of respiratory disorders, e.g., bronchodilators, corticosteroids and drugs for the prophylaxis of asthma. Other drugs such as anorectics, anti-depressants, anti-hypertensive agents, anti-neoplastic agents, anti-cholinergic agents, dopaminergic agents, narcotic analgesics, beta-adrenergic blocking agents, prostaglandins, sympathomimetics, tranquilizers, steroids, vitamins and sex hormones may be employed.

It is preferred that the medicament employed exhibit a potency which permits a single dose to be loaded onto the sheet material in an area of less than about 25 cm² and preferably less than about 5 cm². More preferred is a sheet material containing a drug in such a manner and of such a type that between 0.25 and 2.25 cm², most preferably between 0.5 and 2.0 cm², of the sheet material will contain a single dose when used in a device such as described in said abandoned U.S. application Ser. No. 07/516,328. Stated differently, given that a sheet material of the invention may conveniently carry between about 10 and 150 μg of medicament per cm², the potency of the medicament will preferably be such that a single dose may be carried on the above-stated 0.25 to 2.25 cm² of sheet material.

Exemplary drugs which may be employed in the practice of this invention include:

Salbutamol, terbutaline, rimiterol, fenoterol, pirbuterol, reproterol, adrenaline, isoprenaline, ociprenaline, ipratropium, beclomethasone, betamethasone, budesonide, disodium cromoglycate, nedocromil sodium, ergotamine, salmeterol, fluticasone, formoterol, insulin, atropine, prednisolone, benzphetamine, chlorphentermine, amitriptyline, imipramine, clonidine, actinomycin c, bromocriptine, buprenorphine, propranolol, lacicortone, hydrocortisone, fluocinolone, triamcinolone, dinoprost, xylometazoline, diazepam, lorazepam, folic acid, nicotinamide, clenbuterol, bitolterol, ethinyloestradiol, levonorgestrel and pharmaceutically acceptable salts thereof such as salbutamol sulfate, isoprenaline sulfate, pirbuterol acetate and pirbuterol hydrochloride, to name only a few.

The powdered medicament may be finely micronised by repeated stepwise millings or a closed loop milling system and preferably is in the particle size range of 1 to 10 μm. The medicament may comprise one or more drugs, having one or more particulate forms and may include one or more physiologically acceptable or inert excipients.

While the micronized medicament is generally well held in the depressions without any binders or other excipients, the top surface of the sheet material may be sealed by, for example, a thin polymeric sheet or laminated multilayer sheet to provide additional protection. That polymeric sheet could be removed just prior to the aerosolization step. Additionally or alternatively, storing the sheet material in a rolled-state will in effect seal the top of the depressions through contact with the back-side of the sheet material itself in the next winding of the roll.

Particularly in the case of employment of medicaments which are sensitive to moisture, it may be desirable to incorporate a dessicant material in the sheet material such as in the polymeric material in which the depressions may be formed.

Further, inorganic salts or well-dispersed conductive materials may also be incorporated into the sheet material to lessen any static charge which may build up on the sheet material.

What is claimed is:

1. A flexible sheet material comprising a plurality of discrete depressions in at least one surface thereof, each of said depressions having a depth of about 5 to 500 μm, but less than the thickness of said sheet material, and an opening at the surface of said sheet of about 10 to 500 μm across, a substantial number of said depressions being at least partially filled with micronized medicament, and the area of said surface between said depressions being substantially free of said micronized medicament, wherein said medicament may be aerosolized from said depressions.

2. A flexible sheet material according to claim 1, comprising a polymeric layer in which said depressions are made.

3. A flexible sheet material according to claim 2, wherein said polymeric layer comprises a polymer selected from the group consisting of a polyethylene, a polypropylene, a polyester, a polytetrafluoroethylene and a cellulose.

4. A flexible sheet material according to claim 2, wherein said polymeric layer is laminated or melt-bonded to or extruded onto a support layer.

5. A flexible sheet material according to claim 4, wherein said support layer is selected from the group consisting of a non-woven material, a woven material and a metallized layer.

6. A flexible sheet material according to claim 5, wherein said support layer is a "kraft" paper.

7. A flexible sheet material according to claim 1, wherein said medicament is selected from the group consisting of an antiallergic, a bronchodilator, an antihistamine, a steroid and a mixture of two or more of any of the foregoing.

8. A flexible sheet material according to claim 7, wherein said medicament is selected from the group consisting of albuterol, albuterol sulfate, pirbuterol acetate, pirbuterol hydrochloride, beclomethasone dipropionate, disodium cromoglycate, isoproterenol hydrochloride, isoproterenol sulfate, phenylephrine bitartrate, phenylephrine hydrochloride, epinepherine bitartrate and a mixture of two or more of the foregoing.

9. A flexible sheet material according to claim 1, wherein a substantial number of said recesses contain a physiologically acceptable inert excipient in addition to said medicament.

10. A flexible sheet material according to claim 1, wherein said depressions have a depth of about 5 to 150 μm and an opening at the surface of said sheet material of about 50 to 200 μm across.

11. A flexible sheet material according to claim 1, wherein said depressions number about 500 to 15,000 per $cm^2$ of said sheet material.

12. A flexible sheet material according to claim 1, wherein said depressions are configured in a substantially regular array.

13. A flexible sheet material according to claim 1, having a substantially uniform depression volume per unit area.

14. A flexible sheet material according to claim 1, wherein said depressions are of a configuration selected from truncated cones, truncated pyramids, partial hemispheres and tetrahedrons.

15. A flexible sheet material according to claim 1, wherein a substantial number of said depressions are filled to a controlled depth thereof.

16. A flexible sheet material according to claim 1, wherein a substantial number of said depressions are substantially filled with a known volume of medicament per unit area of said sheet material.

17. A flexible sheet material according to claim 16, wherein an area of about 0.1 to 25 $cm^2$ of said sheet material corresponds to a single dose of said medicament when administered by inhalation.

18. A flexible sheet material according to claim 1 in the form of a tape.

19. An article comprising a flexible sheet material according to claim 16 wound on a spool or in the form of a roll.

20. A flexible sheet material according to claim 1, wherein said medicament may be aerosolized from said depressions in a substantially deagglomerated state for inhalation by a patient.

21. A cassette comprising a housing, a sheet material according to claim 1 in the form of a rolled tape, and a tape advance control mechanism to provide uniform tape advance.

22. A flexible sheet material according to claim 1, wherein said depressions are formed by an imprinting process comprising pressing the sheet material against a master surface bearing protuberances of appropriate size and shape to form the depressions, said process optionally involving heating of said sheet material to a temperature less than about the melting point of any polymeric layer in which said depressions are being made.

* * * * *